United States Patent
Trumm et al.

(10) Patent No.: US 10,161,828 B2
(45) Date of Patent: Dec. 25, 2018

(54) METHOD FOR CALIBRATING A POLARISATION AXIS MEASURING DEVICE AND METHOD FOR DETERMINING POLARISATION AXES OF SPECTACLE LENSES FOR A POLARISATION AXIS MEASURING DEVICE

(71) Applicant: RODENSTOCK GMBH, München (DE)

(72) Inventors: Stephan Trumm, München (DE); Johann Auer, Regen (DE); Werner Müller, Ötisheim (DE)

(73) Assignee: RODENSTOCK GMBH, München (DE)

( * ) Notice: Subject to any disclaimer, the term of this patent is extended or adjusted under 35 U.S.C. 154(b) by 0 days.

(21) Appl. No.: 15/558,106

(22) PCT Filed: Apr. 15, 2016

(86) PCT No.: PCT/EP2016/058436
§ 371 (c)(1),
(2) Date: Sep. 13, 2017

(87) PCT Pub. No.: WO2016/169862
PCT Pub. Date: Oct. 27, 2016

(65) Prior Publication Data
US 2018/0052074 A1   Feb. 22, 2018

(30) Foreign Application Priority Data

Apr. 20, 2015   (DE) .................. 10 2015 106 041

(51) Int. Cl.
*G01J 4/00*       (2006.01)
*G01M 11/02*   (2006.01)
(Continued)

(52) U.S. Cl.
CPC .... *G01M 11/0207* (2013.01); *G01M 11/0221* (2013.01); *G01N 21/19* (2013.01);
(Continued)

(58) Field of Classification Search
CPC ............... G01N 21/8507; G01N 21/31; G01N 21/0303; G01N 21/59; G01N 21/05
(Continued)

(56) References Cited

U.S. PATENT DOCUMENTS

| 5,260,827 A | 11/1993 | Dziekan |
| 2002/0158985 A1 | 10/2002 | Saitoh et al. |

(Continued)

FOREIGN PATENT DOCUMENTS

| CN | 202024877 U | * 11/2011 |
| CN | 202024877 U | 11/2011 |

(Continued)

OTHER PUBLICATIONS

International Preliminary Report on Patentability and the Written Opinion of the International Searching Authority (Forms PCT/IB/338, PCT/IB/326, PCT/IB/373 and PCT/ISA/237), dated Nov. 2, 2017, for International Application No. PCT/EP2016/058436, with an English translation.

(Continued)

*Primary Examiner* — Md M Rahman
(74) *Attorney, Agent, or Firm* — Birch, Stewart, Kolasch & Birch, LLP

(57) ABSTRACT

In a method for calibrating a polarization axis measuring device, both flat sides of a calibration element in a polarization axis measuring device are irradiated with polarized light, wherein the method involves aligning in each case at least one polarization direction of the light in a first and/or second rotational position with a principal axis in a predefined angular relationship with respect to a polarization (Continued)

axis of the calibration element. Determining the rotational position of an axis of the calibration element is carried out by determining an angle bisector between the first and second rotational positions of the polarization direction of the incident light. The method involves assigning a predefined angle value for the rotational position of the principal axis of the polarization direction for which the latter is in the predefined angular relationship with respect to the axis of the calibration element inserted as intended. Furthermore, the invention relates to a method for determining polarization axes of spectacle lenses, to a calibration element, and to a polarization axis measuring device comprising a calibration element.

30 Claims, 6 Drawing Sheets

(51) Int. Cl.
  *G01N 21/19* (2006.01)
  *G01N 21/21* (2006.01)
  *G01N 21/27* (2006.01)

(52) U.S. Cl.
  CPC ............ *G01N 21/21* (2013.01); *G01N 21/274* (2013.01); *G01N 21/278* (2013.01)

(58) Field of Classification Search
  USPC ......................................................... 356/364
  See application file for complete search history.

(56) References Cited

U.S. PATENT DOCUMENTS

| | | | |
|---|---|---|---|
| 2008/0088828 A1 | 4/2008 | Ham et al. | |
| 2008/0284677 A1* | 11/2008 | Whitehead | G09G 3/20 345/1.3 |
| 2010/0045956 A1* | 2/2010 | Van De Kerkhof | G01M 11/0264 355/71 |
| 2014/0055664 A1 | 2/2014 | Yamagata et al. | |
| 2015/0355027 A1* | 12/2015 | Beghuin | G01J 3/4537 356/453 |

FOREIGN PATENT DOCUMENTS

| | | |
|---|---|---|
| DE | 1610310 U | 3/1950 |
| JP | 58-127184 A | 7/1983 |
| JP | 5-180697 A | 7/1993 |
| JP | 2000-171631 A | 6/2000 |
| JP | 2005-227019 A | 8/2005 |
| JP | 2006-242617 A | 9/2006 |
| JP | 2010-32831 A | 2/2010 |
| WO | WO 01/65306 A1 | 9/2001 |

OTHER PUBLICATIONS

International Search Report (PCT/ISA/210) issued in PCT/EP2016/058436, dated Jun. 30, 2016.
English translation of the Japanese Notification of Reasons of Rejection for corresponding Japanese Application No. 2017-546828, dated Oct. 2, 2018.

* cited by examiner

METHOD FOR CALIBRATING A POLARISATION AXIS MEASURING DEVICE AND METHOD FOR DETERMINING POLARISATION AXES OF SPECTACLE LENSES FOR A POLARISATION AXIS MEASURING DEVICE

PRIOR ART

The invention relates to a method for calibrating a polarisation axis measuring device, a method for determining polarisation axes of spectacle lenses, a calibration element for a polarisation axis measuring device, and a polarisation axis measuring device.

Polarisation axis measuring devices are employed in the field of spectacle optics, in order to determine and to check the orientation the polarisation plane in the case of polarising spectacle lenses. Undesirable dazzling reflections, such as occur for example on water surfaces, can be suppressed by polarising lenses. To a lesser extent this also occurs for sunlight scattered on the atmosphere, so that these lenses act to a certain degree to increase contrast. When reflected on non-metallic surfaces, predominantly the proportion of the light of which the direction of polarisation is perpendicular to the plane of incidence is actually reflected at suitable angles. Accordingly a spectacle lens should suppress horizontally polarised light.

For measurement of the polarisation axis, i.e. orientation of the polarisation plane, of a polarising spectacle lens, it is usual to operate a method which follows the relevant standard DIN EN ISO 8980-3:2014-03. Such polarisation axis measuring devices are usually calibrated with a calibration body made from polarising material with a known orientation of the polarisation plane. The production of such calibration bodies is complex and the method of calibration is susceptible to systematic faults.

In this case the intersection of the polarisation plane of linearly polarised transmitted light with the plane of a test piece or of a polariser is designated as the polarisation axis. The polarisation plane is defined as the plane which is perpendicular to the oscillation plane of the electrical field of the light wave. However, the oscillation direction of the electrical field of the light wave is given as the direction of polarisation. The plane of incidence is the plane which is spanned by the direction of propagation of the incident light as well as the perpendicular to the reflecting surface. Thus it also contains the direction of propagation of the reflected light.

DISCLOSURE OF THE INVENTION

The object of the invention is to provide a method for calibration of a polarisation axis measuring device with such a calibration element, which enables precise and reproducible calibration.

A further object of the invention is to create a method for determining polarisation axes of spectacle lenses with such a polarisation axis measuring device which enables reproducible determination of the polarisation axes.

A further object of the invention is to provide a calibration element for a polarisation axis measuring device, which calibration element is simple to produce and allows precise calibration of a polarisation axis measuring device by such a method for calibration of a polarisation axis measuring device.

A further object of the invention is to provide a polarisation axis measuring device with such a calibration element, which is simple to produce and allows precise calibration of the polarisation axis measuring device.

These objects are achieved by the features of the independent claims. Advantageous embodiments and advantages of the invention are apparent from the further claims, the description and the drawings.

According to one aspect the invention relates to a method for calibrating a polarisation axis measuring device with a calibration element, comprising the steps (i) insertion of a calibration element into the polarisation axis measuring device and irradiation of a first flat side of the calibration element with polarised light, (ii) aligning at least one polarisation direction of the light in a first rotational position with a principal axis in a predefined angular relationship with respect to a polarisation axis of the calibration element, (iii) insertion of the calibration element and irradiation of the second flat side thereof with polarised light, (iv) aligning the at least one polarisation direction of the light in a second rotational position with the principal axis in a predefined angular relationship with respect to the polarisation axis of the calibration element, (v) determining the rotational position of an axis of the calibration element by determining an angle bisector between the first and second rotational positions of the polarisation direction of the incident light, and (vi) assigning a predefined angle value for the rotational position of the principal axis of the polarisation direction for which the latter is in the predefined angular relationship with respect to the axis of the calibration element inserted as intended.

In a first embodiment a polariser can be employed in combination with a light source which emits unpolarised light transmits. Instead, in an alternative embodiment at least one light source can be employed which emits polarised light.

The predetermined angular relationship can be a parallel or perpendicular alignment of the principal axis with respect to the polarisation axis of the calibration element.

In an embodiment of the method, the insertion of the calibration element into the polarisation axis measuring device can take place with the first flat side thereof directed towards the polariser, which is irradiated with unpolarised light, and for alignment of the polarisation direction an alignment of the polariser in a first rotational position of the polariser with a principal axis can take place in a predefined angular relationship with respect to a polarisation axis of the calibration element and/or alignment of a receptacle for the calibration element, wherein light is transmitted from the first flat side through the calibration element. The insertion of the calibration element can take place with the second flat side directed towards the polariser, and for alignment of the polarisation direction the alignment of the polariser in a second rotational position of the polariser with the principal axis can take place in the predefined angular relationship with respect to the polarisation axis of the calibration element and/or the alignment of the receptacle for the calibration element, wherein light is transmitted from the second flat side through the calibration element.

Determining the rotational position of the axis of the calibration element can be carried out by determining an angle bisector between the first and second rotational positions of the polariser.

In one embodiment the polariser can be arranged rotatably about an optical axis. Alternatively a receptacle which receives the calibration element can also be arranged rotatably about the optical axis. Alternatively both the polariser and also the receptacle can be rotatable about the optical axis rotatable.

In the predetermined angular relationship the principal axis can advantageously be aligned parallel or perpendicular to the polarisation axis of the calibration element. However, in principle a different angular relationship is also conceivable. In this case the rotational position of the principal axis of the polariser is assigned a predefined angle value with which it is in the predefined angular relationship with respect to the axis of the calibration element inserted as intended.

In this case the predefined angle value does not have to correspond to the angular relationship predefined by the calibration. The predefined angular relationship relates to the adjustment process during the calibration. If an angular offset exists between the axis of the calibration element and the principal axis of the polariser, this angular offset can be taken into consideration in the calibration as a fixed angular relationship. Furthermore, the predefined angle value can include an angular relationship in the adjustment during the measurement of the test piece.

The calibration consists of establishing a relationship between a defined position of the principal axis of the polariser and an axis of the receptacle with the aid of a calibration element. A polariser with an undivided field of view can be used, wherein the polarisation axis constitutes the principal axis. Alternatively a polariser with a divided field of view can be used, wherein two regions with different polarisation axes adjoin the principal axis. Light passing through the polariser with a divided field of view has for example two polarisation directions. Alternatively, instead of the polariser with an undivided field of view a light source with polarised light can be employed. Instead of the polariser with a divided field of view two light sources with polarised light can be employed, the polarisation axes of which are symmetrical with the principal axis.

In contrast to the prior art, in which for this purpose a polariser with known alignment of the polarisation axis, instead of the test piece, is usually introduced as a calibration body into the device, the polariser is adjusted to maximum cancellation of both fields of view or, in the simplified method, to the minimum or maximum transmitted light intensity, and the known position of the polarisation axis of the calibration body is assigned to the alignment of the principal axis of the polariser achieved after this adjustment, in the method according to the invention the precise position of the polarisation axis of the calibration body does not need to be known.

In fact, in the procedure according to the invention the absolute orientation of the polarisation axis of the calibration body has no influence on the calibration result.

This is achieved in that the calibration body is measured twice by the as yet uncalibrated polarisation axis measuring device, wherein between the first and the second measurement it is rotated, i.e. turned, by 180° about an axis lying in the plane of the polariser (or the at least one light source with polarised light), namely the axis of the calibration element, so that once a first flat side faces the polariser and once a second flat side faces the polariser. As a result a deviation of the position of the polarisation axis of the calibration body from the axis of the calibration element in both measurements leads to deviations by equal absolute values in the respective measurement results, which cancel each other out in the subsequent arithmetic averaging of the rotational position of the principal axis of the polariser.

The determination of the rotational positions can be carried out multiple times in each case and the respective measured values can be taken as average values of the individual measurements, in order to improve the statistical measurement uncertainty.

According to an advantageous embodiment a polariser with divided field of view can be used which comprises at least a first region with a first polarisation axis as well as a second region with a second polarisation axis, wherein the first polarisation axis and the second polarisation axis have with respect to the principal axis an angle which is the same in terms of absolute value with opposite plus/minus signs, wherein the angle is preferably between 2° and 5°, particularly preferably between 2.5° and 3.5°, especially preferably 3°. In this case it is not so much the exact absolute value of the angle which is crucial but rather the fact that the absolute values are the same.

According to an advantageous embodiment an alignment of the principal axis of the polariser (or the light sources with polarised light) can take place by equalising a light intensity transmitted by the first region of the polariser with a first polarisation axis and a light intensity transmitted by the second region of the polariser with a second polarisation axis at the same brightness, in particular at a low brightness.

The case of minimal transmission is advantageously chosen, since the human eye has a logarithmic sensitivity and therefore small differences in the brightness of two dark fields can be perceived more accurately than differences in the brightness of two bright fields. An automatic measured value acquisition with an analysis unit which measures the transmitted light intensity through the optional mirror or without the use of the optional mirror, can operate both with equalisation at both minimum and maximum brightness.

According to an advantageous embodiment a polariser with an undivided field of view can be used which comprises at least one region with a polarisation axis, wherein the polarisation axis forms the principal axis. In this case a division of the polariser can be omitted. In this case the advantage consists in a simpler and more cost-effective design of the polariser.

According to an advantageous embodiment an alignment of the principal axis of the polariser (or the at least one light source with polarised light) can take place by minimising or maximising a light intensity transmitted by a region of the polariser with a polarisation axis. In this embodiment the division of the polariser is omitted. In this case the advantage consists in a simpler and more cost-effective design of the polariser.

Advantageously in this case the polarisation axis of the polariser corresponds to the principal axis thereof.

For measurement, there is an adjustment to the minimum or maximum of the transmitted light intensity. Such an embodiment is very suitable in particular for automated methods in which the transmitted light intensity can be detected by a sensor for different angular positions.

A pre-calibration in the form of an angle calibration of the rotatably arranged polariser is preferably carried out before the method according to the invention for calibration of the polarisation axis measuring device. In the pre-calibration an arbitrarily selected setting/position of the polariser (or of the at least one light source with polarised light) has associated with it a likewise arbitrarily selected angle value. Thus a display of the angular position of the polariser (or of the at least one light source with polarised light) is provided, which can be used during the calibration process according to the invention for determining the polarisation axis of the calibration element.

According to an advantageous embodiment of the method according to the invention for calibration of a polarisation axis measuring device, a zero value can be assigned to a third rotational position of the principal axis of the polariser (or of the at least one light source with polarised light) in which it is in the predefined angular relationship with respect to the axis of the calibration element inserted as intended. This third position of the polariser (or of the at least one light source with polarised light) advantageously corresponds to an axis defined by markings on the receptacle of the polarisation measuring device.

Thus advantageously there is a direct assignment of angle degrees as the angular distance of the polarisation axis of the test piece to the axis defined by the markings of the receptacle, which enables an advantageous registration and evaluation of the measurement results of the determination of the polarisation axes.

If the axis predefined by the receptacle for the calibration element and the axis predefined by markings for alignment of the test pieces do not correspond, the difference between these two axis positions can be taken into consideration in the assignment of the calibration value. Advantageously in this case the value zero corresponds to the alignment of the principal axis of the polariser parallel or perpendicular to the axis predefined by the marking of the support for the test pieces.

According to a further aspect the invention relates to a method for determining polarisation axes of spectacle lenses. In this case spectacle lenses can comprise round blanks, custom-shaped lenses or can be ready mounted in frames, or pairs of spectacle lens and spectacle lens blanks. The method comprises the calibration of a polarisation axis measuring device according to the method described above.

Furthermore, the method comprises the oriented insertion of a spectacle lens into a receptacle of the polarisation axis measuring device by alignment with a marking of the receptacle, the alignment of a principal axis in a predefined angular relationship with respect to the polarisation axis of the spectacle lens and thus the subsequent determination of the angular difference of the rotational position of the polariser and the marking of the receptacle and, following therefrom, the determination of the polarisation axis of the spectacle lens relative to an orientation of the spectacle lens.

The method according to the invention for determining polarisation axes of spectacle lenses can be used in the field of spectacle optics, in order to determine and to check the alignment of the polarisation plane in the case of polarising spectacle lenses, in particular in the quality control. With the method a polarisation axis of a spectacle lens can be reliably and reproducibly determined, since the polarisation axis measuring device has been previously calibrated reliably and reproducibly with the aid of the calibration element, wherein the calibration element is simple to produce. In this case the precision of the measurement can be increased by multiple executions and thus a corresponding improvement of the statistics. If necessary the quality of the calibration can also be checked by a repeated measurement of the calibration element and thus the polarisation axis measuring device can also be recalibrated if necessary.

For measurement of assembled spectacle lenses the markings for alignment of the spectacle lenses can be a contact rail, against which the frame in which the lenses are fitted can be laid and which can correspond to the horizontal of the frame.

Advantageously the predetermined angular relationship can in particular comprise a parallel or perpendicular alignment of the principal axis with respect to the polarisation axis of the spectacle lens.

According to a further aspect of the invention a calibration element is proposed which is intended for insertion into a receptacle in a polarisation axis measuring device which is designed and intended for carrying out the method according to the invention.

The calibration element comprises a translucent calibration body made of polarising material, the calibration body, with a first and an opposing second flat side, as well as a holder for holding the calibration body, which holder has at least one positioning device for reproducible arrangement as intended in a receptacle.

In this case the holder has a transilluminated region for transillumination of the calibration body with light. The positioning device has at least two diametrically opposing positioning elements, wherein the holder with the calibration body can be inserted selectively with its first flat side or with its second flat side into the receptacle of the polarisation axis measuring device. The holder for holding the calibration body and the calibration body itself can form a component, wherein the holder can preferably form an edge region of the calibration body.

In the simplest case the calibration element according to the invention comprises a piece of polarising material which can be shone through by a light source. The calibration element is provided with a positioning device which enables a precise alignment of the calibration element in the polarisation axis measuring device. In this case for example the calibration body is fitted into a frame which is provided with markings for correct contact, or the calibration body is directly provided with these markings. The advantage in this case is that an axis of the calibration body, which axis lies in the plane of the calibration body, is predefined by the markings and a precise alignment of the marking with respect to the polarisation axis of the calibration body is not necessary.

Particularly advantageously the calibration element is provided with a mechanical positioning device, which enables a correct and precise alignment of the calibration body with respect to the polarisation axis measuring device, preferably prevents turning out of position of the calibration body within its plane about its vertical axis perpendicular to the plane, and in particular only allows turning about the axis of the calibration body by 180°. In this case the mechanical positioning device can take on the function of the markings.

Advantageously in this case the positioning device is configured so that, as intended, the holder can be arranged in the receptacle so as to be rotation-proof about an optical axis of the polarisation axis measuring device.

According to an advantageous embodiment the positioning device can have at least one pin as positioning element, which projects both over the first flat side and also over the second flat side. With one or more such pins, which can be configured as locating pins, the holder of the calibration element with the calibration body is inserted selectively with its first flat side or with its second flat side into the receptacle of the polarisation axis measuring device.

In this case this positioning of the calibration element in the polarisation axis measuring device is possible very reliably and reproducibly, so that calibration inaccuracies in the measurement can be largely precluded.

According to an advantageous embodiment the positioning device can have at least one opening as positioning element.

As an alternative to the embodiment with locating pins in the holder of the calibration element, the locating pins can also be provided in the receptacle of the polarisation axis measuring device, and in the holder of the calibration element openings are advantageously provided into which the locating pins can then be introduced as intended, so that in this case positioning of the calibration element in the polarisation axis measuring device is possible very reliably and reproducibly.

According to an advantageous embodiment the positioning device can have at least one marking, such as for instance a notch or a line mark, as positioning element. Such a marking can also be a further efficient possibility for positioning the calibration element precisely and reproducibly in the polarisation axis measuring device.

According to an advantageous embodiment the positioning device can have at least one contact edge as positioning element. In this case the contact edge preferably forms a component of the periphery of the holder, and thus is for example configured as a milled edge on the periphery of the holder. The contact edge could also be fitted as a rail onto the holder of the calibration element. Such a contact means can be a further efficient possibility for positioning the calibration element precisely and reproducibly in the polarisation axis measuring device.

Alternative possibilities for reliable and reproducible positioning of the calibration element in the receptacle of the polarisation axis measuring device are conceivable for example in combinations of the aforementioned positioning elements. Thus for example the holder of the calibration element can alternatively have two locating pins, or two openings.

The openings or locating pins are preferably configured in such a way that rotation or rotated insertion of the calibration element by 180° about a vertical axis of the calibration element is prevented. In order to achieve this, the openings or the locating pins can be configured for example with different sizes. If openings or locating pins of equal size are provided in each case, the holder preferably has further openings or locating pins and/or markings which are arranged in such a way that an unambiguous insertion of the calibration element is made possible.

Furthermore, the holder can comprise combinations of different positioning elements. The corresponding counter-elements can be provided in each case in the receptacle of the polarisation axis measuring device.

According to an advantageous embodiment the calibration body can have a translucent region with a polarisation axis. The calibration element can advantageously have a calibration body made from a polarising material with a polarisation axis. In this case it is advantageous if the calibration body is designed to be translucent at least in one region, so that the calibration element can be brought into a light beam of the polarisation axis measuring device and the transmitted light intensity can be used for calibration.

According to a further aspect the invention relates to a polarisation axis measuring device with such a calibration element, wherein the polarisation axis measuring device is constructed and intended for carrying out the method according to the invention, and the calibration element comprises a light source with unpolarised light, a polariser arranged rotatably about an optical axis and having a principal axis, as well as a receptacle for a test piece. The rotatably arranged polariser is also designated as a measurement polariser.

In this case the calibration element comprises a translucent calibration body made of polarising material, as well as a holder for holding the calibration body, wherein the holder has at least one positioning device for reproducible arrangement in the receptacle. In this case the calibration element is directed selectively with a first flat side or with a second flat side towards the polariser and is arranged as a test piece in the receptacle.

Alternatively, instead of the polariser with unpolarised light at least one light source with a principal axis can be used which emits polarised light. Alternatively a receptacle which receives the calibration element can also be arranged rotatably about the optical axis.

The polarisation axis measuring device according to the invention serves for measurement of the precise position of the polarisation axis of polarising material, such as is used for example in lenses for polarising sunglasses.

Advantageously a mirror can also be provided for observation of a light intensity which is transmitted by the light source parallel to the optical axis through the polariser and the test piece, and which enables an ergonomically advantageous operation of the polarisation axis measuring device, since the user does not have to bend over the apparatus, but can view the mirror image of the test piece from the front in the suitably aligned mirror.

The basis for the measurement principle is that as linearly polarised light passes through polarising media the intensity of the transmitted light depends substantially upon the angle between the polarisation plane of the light and the polarisation axis of the material.

For this purpose the light from a light source which is not polarised a priori is polarised by a polariser. Since the polariser is advantageously mounted on precision rotary mount, the polarisation direction can be predefined. The light polarised in such a way passes through the test piece. Of the light thus polarised, only the component which corresponds to the position of its polarisation axis is allowed to pass through the test piece. If the polarisation axes of both components are parallel to one another, the transmission is at a maximum (and in the case of ideal components is complete), if they are perpendicular, the transmission is at a minimum (and in the case of ideal components complete cancellation occurs).

At the start of the measurement the test piece is brought into a defined position in which it remains fixed during the measurement. In this case the test piece is preferably arranged so that only during the measurement it cannot be moved, but after the measurement it can be easily removed from the receptacle. However, a simple support is conceivable in which the test piece is not rotated but in principle could be rotated. The light source is then viewed through the test piece and the polariser and the polariser is aligned with a rotary mounting so that the least possible light passes through the combination of polariser and test piece.

The polarisation axis measuring device according to the invention enables autonomous calibration. This means that the polarisation axis measuring device can be calibrated without the aid of pre-calibrated objects or instruments. According to the invention a calibration body with polarising action, for example a polarisation film, is used, of which the polarisation axis also does not have to be known a priori. An axis located in the plane of the calibration element, and about which the calibration element can be turned, is marked on the calibration element.

This marking is visible from both flat sides which can be arbitrarily fixed. The axis of the calibration element can be chosen arbitrarily and must does not have to correspond either to the polarisation axis or to a geometric axis of symmetry. For example, the axis can be provided by the connecting axis of two locating pins. Moreover, by turning of the calibration element it is ensured that systematic measurement errors can also be compensated for.

In order to achieve calibration which is as precise as possible, advantageously there is no single adjustment to the disappearance of the contrast during support of the test piece with a known polarisation axis, but with a rotary mounting of the rotatably arranged polariser a "zero position", which results from the averaging of a plurality of measurements, is approached with reference to the display. As a result, the inaccuracy in the measurement of the axis of the calibration body, caused for example by the inaccuracy in setting the rotary mounting during the calibration process, which is manifested as a systematic error in later measurements based on the calibration thus achieved, can be reduced from the statistical inaccuracy of one measurement to the measurement uncertainty of a series of measurements.

Instead of a simple polariser, as described in the corresponding standard DIN EN-ISO-8980-3:2014-03 from the year 2014, a polariser with a divided field of view, namely two regions with polarisation axes aligned differently from one another, can be used. This usually consists of two semi-circular polarisation elements. The boundary between the two fields of view is designated as the principal axis.

According to an advantageous embodiment the polariser can comprise at least a first region with a first polarisation axis as well as a second region with a second polarisation axis, wherein the first polarisation axis and the second polarisation axis have with respect to the principal axis an angle which is the same in terms of absolute value with opposite plus/minus signs, wherein the angle is preferably between 2° and 5°, particularly preferably between 2.5° and 3.5°, especially preferably 3°. In this case it is not so much the exact absolute value of the angle which is crucial but rather the fact that the absolute values are the same.

As an alternative to the polariser with a divided field of view with the two polarisation axes aligned differently from one another, it is also possible to use polarised light with two polarisation axes aligned differently from one another, for example from two light sources which emit polarised light. In this case the principal axis constitutes the angle bisector between the two polarisation axes.

With the optional mirror the light source can be viewed through the test piece, wherein the light is polarised by the polariser through the two regions of the polariser with divided field of view. In this case the observed brightness depends upon the relative position of the principal axis as the angle bisector between the two polarisation axes of the polariser with respect to the polarisation axis of the test piece. For the measurement an adjustment is made to the disappearance of the contrast between the two fields of view in the case of maximum cancellation. Since the brightness of the two fields of view at the boundary is directly discernible, in spite of the manual procedure a high precision and reliability of the measurement can be achieved. After a corresponding calibration the angle of the polarisation axis of the test piece can now be read off directly on the digital display of a connected rotary encoder.

According to an advantageous embodiment the polariser can alternatively comprise at least one region with a polarisation axis. In this case the polarisation axis forms the principal axis of the polariser. In this embodiment the division of the polariser is omitted.

In this case the advantage consists in a simpler and more cost-effective design of the polariser. In this case the polarisation axis of the polariser is specified as the principal axis thereof. For measurement, there is an adjustment to the minimum or maximum of the transmitted light intensity. Such an embodiment is very suitable for automated methods in which the transmitted light intensity can be detected by a sensor for different angular positions.

The invention further relates to a computer program product for calibration of a polarisation axis measuring device, comprising a computer-readable memory medium containing a program code which is designed to carry out the method according to the invention for calibration of a polarisation axis measuring device if the program code is executed on a data processing unit. The computer program product can be used for example in a computer which is coupled to the polarisation axis measuring device.

The invention also relates to a computer program product for determination of polarisation axes of spectacle lenses, comprising a computer-readable memory medium containing a program code which is designed to carry out the method according to the invention for determination of polarisation axes of spectacle lenses if the program code is executed on a data processing unit.

The computer program product can be used for example in a computer which is coupled to a corresponding measuring device for determination of polarisation axes of spectacle lenses.

DRAWINGS

Further advantages are apparent from the following description of the drawings. Embodiments of the invention are illustrated in the drawings. The drawings, the description and the claims contain numerous features in combination. The person skilled in the art will also advantageously consider the features individually and produce further sensible combinations thereof.

In the drawings, by way of example:

EMBODIMENTS OF THE INVENTION

Figure 1:
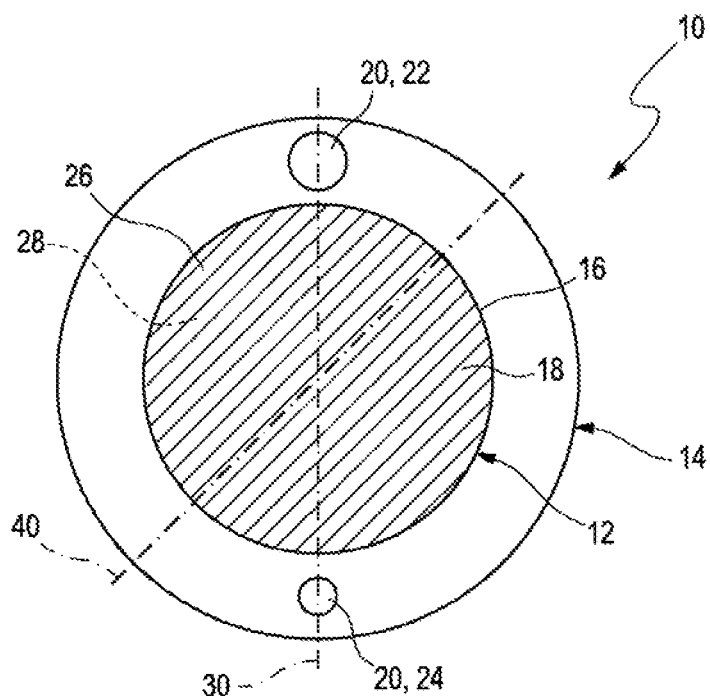
FIG. 1 shows a plan view of a calibration element according to an embodiment of the invention with two locating pins as positioning elements.

In the drawings similar or equivalent components are provided with the same reference signs. The drawings show only examples and should not be understood as limiting.

FIG. 1 shows a plan view of a calibration element 10 according to an embodiment of the invention with two locating pins as positioning elements 22, 24. The calibration element 10 for insertion into a receptacle 108 of a polarisation axis measuring device 100 (illustrated in FIG. 6) comprises a translucent calibration body 12 made of polarising material with a first and an opposing second flat side 26, 28, in particular a front side 26 and a back side 28. Furthermore, the calibration element 10 comprises a holder 14 for holding the calibration body 12, which holder 14 is configured in FIG. 1 in the form of a ring and has at least one positioning device 20 for reproducible arrangement as intended in a receptacle 108. In the exemplary embodiment in FIG. 1 the positioning device 20 has locating pins with different diameters as positioning elements 22, 24, which project both over the first flat side 26 and also over the second flat side 28, so that the holder 14 can be arranged in a rotation-proof manner about an optical axis of a polarisation axis measuring device in a receptacle. The holder 14 has a transillumination region 16 for transillumination of the calibration body 12 with light.

The positioning device 20 has at least two diametrically opposed positioning elements 22, 24, 32, 34, 42 (see FIGS. 1, 3, 4, 5). The holder 14 with the calibration body 12 can be inserted as required with its first flat side 26 or with its second flat side 28 into the receptacle 108 of the polarisation axis measuring device 100. The calibration body 12 has a translucent region 18 with a polarisation axis 40. The two positioning elements 22, 24 are arranged on an axis 30 of the calibration body 12 (illustrated in FIG. 1), the calibration body 12 is turned about the axis 30 and can be inserted into the receptacle 108 of the polarisation axis measuring device 100. The polarisation axis 40 of the calibration body 12 is shown in FIGS. 1 to 5. The hatching of the calibration body 12 should indicate the polarisation direction thereof.

Figure 2:
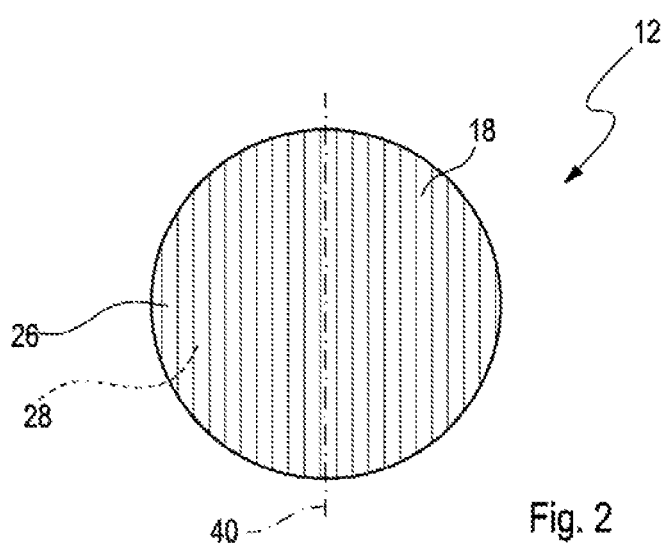
FIG. 2 shows the calibration body made of polarisable material of the calibration element of FIG. 1.

The calibration body 12 made of polarisable material of the calibration element 10 of FIG. 1 is illustrated separately in FIG. 2. In the simplest case the calibration body 12 can be formed from a polarisable film which can be for example glued to a holder 14, in order thus to maintain a fixed orientation on the calibration element 12. Alternatively the holder 14 and the calibration body 12 can form a component, and preferably the holder 14 can form an edge region of the calibration body 12.

Figure 3:
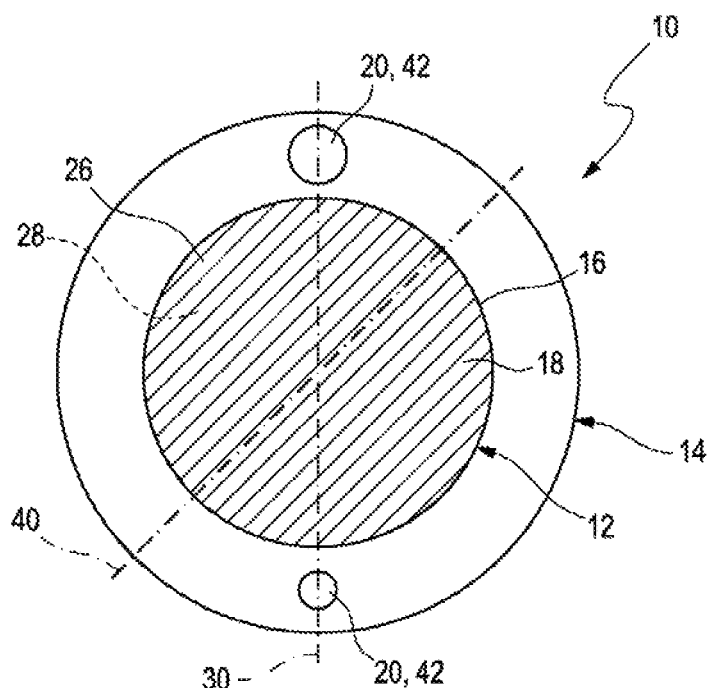
FIG. 3 shows a plan view of a calibration element according to another embodiment of the invention with two openings as positioning elements.

Furthermore FIG. 3 shows a plan view of a calibration element 10 according to another exemplary embodiment of the invention with two openings as positioning elements 42. An embodiment with two openings in the holder 14 of the calibration element 10 is particularly advantageous if corresponding complementary locating pins are provided in the receptacle 108 of the polarisation axis measuring device 100. In this way the calibration element 10 can be inserted with a first flat side 26 or a second flat side 28 into the receptacle 108.

Figure 4:
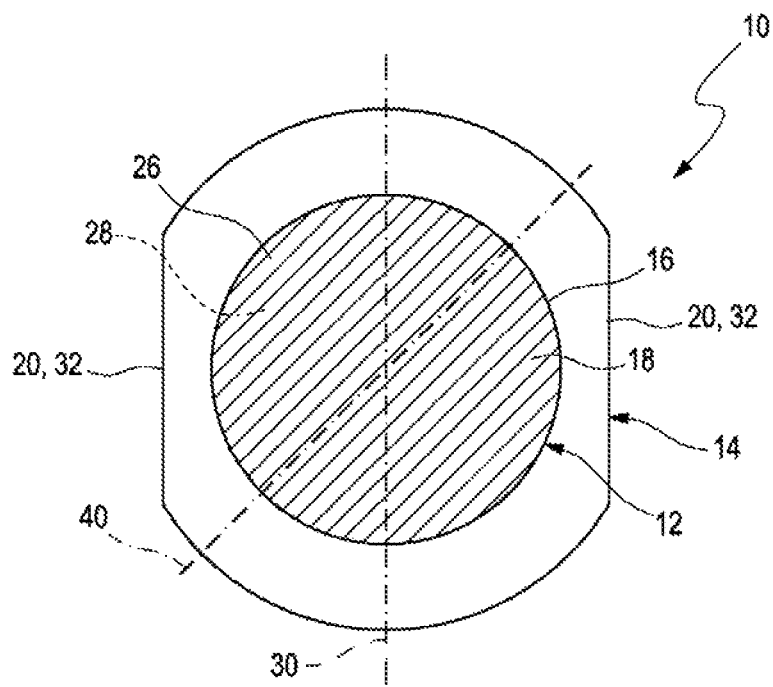
FIG. 4 shows a plan view of a calibration element according to a further embodiment of the invention with two contact edges as positioning elements.

FIG. 4 shows a plan view of a calibration element 10 according to a further exemplary embodiment of the invention with two contact edges 32 as positioning means 20. The contact edge 32 preferably forms a component of the circumference of the holder 14. The contact edge 32 can be constructed for example as a milled edge of the holder 14. Also with the aid of such contacts 32 the calibration element 10 can be reproducibly inserted with a first flat side 26 or a second flat side 28 into the receptacle 108.

Figure 5:
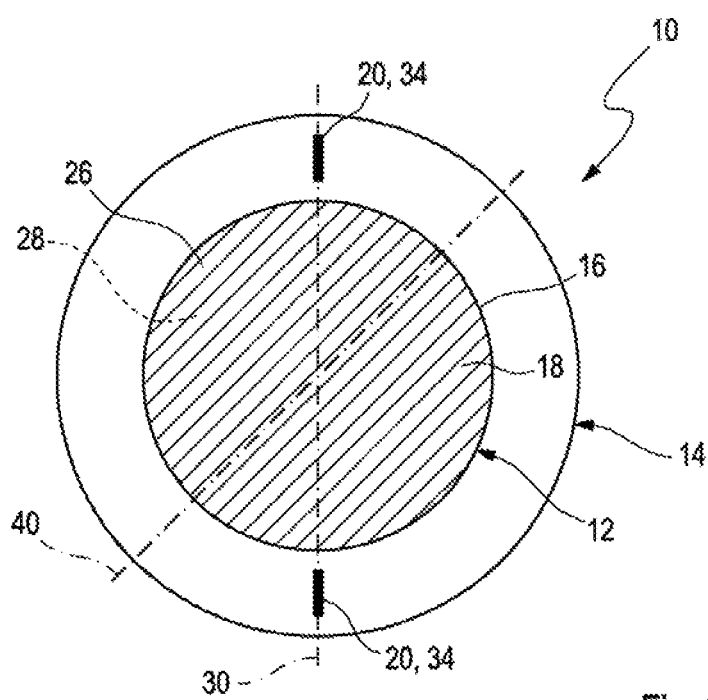
FIG. 5 shows a plan view of a calibration element according to a further embodiment of the invention with two markings as positioning elements.

FIG. 5 shows a plan view of a calibration element 10 according to a further exemplary embodiment of the invention with two markings 34 as positioning means 20. With the aid of such markings 34 the calibration element can be aligned on corresponding markings 132, which are applied in the receptacle 108 (illustrated in FIG. 7), during insertion into the receptacle 108. Also in this way a reproducible arrangement in the receptacle 108 is possible, in order thus to obtain reliable measured values.

Figure 6:
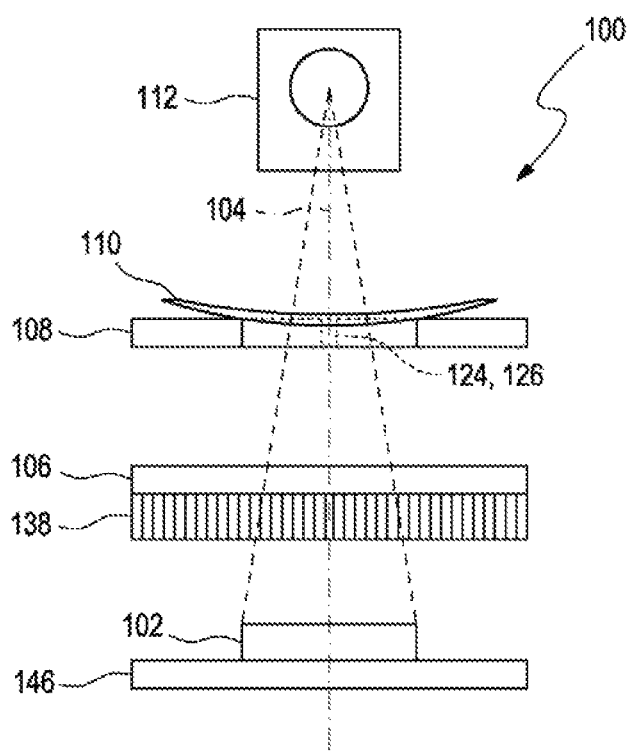
FIG. 6 shows a schematic representation of a polarisation axis measuring device according to an exemplary embodiment of the invention.

FIG. 6 shows a schematic representation of a polarisation axis measuring device 100 according to an exemplary embodiment of the invention. The polarisation axis measuring device 100 comprises a light source 102 with unpolarised light, a polariser 106 with a principal axis 134 arranged rotatably about an optical axis 104 (illustrated in FIG. 9), a receptacle 108 for a test piece 110, as well as a mirror 112 for visual equalisation of the light intensity transmitted by the light source 102 parallel to the optical axis 104 through the polariser 106 and the test piece 110 by adjustment of the polariser 106 arranged rotatably in a rotary mounting 138. In this case the receptacle 108 has counter-elements 124 for example in the form of two openings 126, 128 (illustrated in FIG. 7) for the insertion of the calibration element 10 into the receptacle 108 with the aid of the positioning device 20. The mounted mirror 112 is inclined towards the operator of the polarisation axis measuring device 100, so that the operator sees a mirror image of the test piece 110. The mirror 112 increases the ergonomics of the polarisation axis measuring device 100. It enables the user to operate the device completely from the front, without having to bend over the apparatus as the test piece 110 is placed or during the measuring operation.

Since the test piece 110 itself rests in a fixed position, spectacle lenses which are already held can be measured. For this purpose the device can be augmented with a corresponding stop for the spectacle frame.

Figure 8:
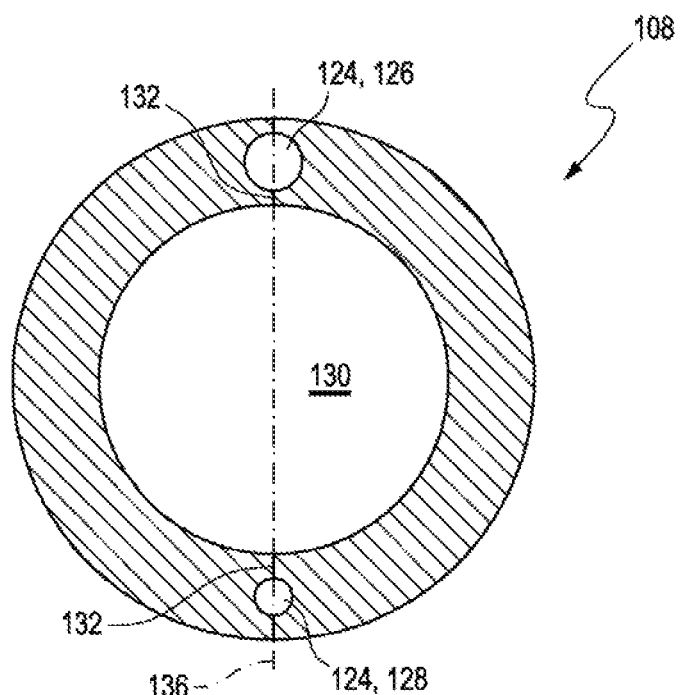
FIG. 8 shows a plan view of a receptacle of a test piece of a polarisation axis measuring device according to an exemplary embodiment of the invention.
Figure 9:
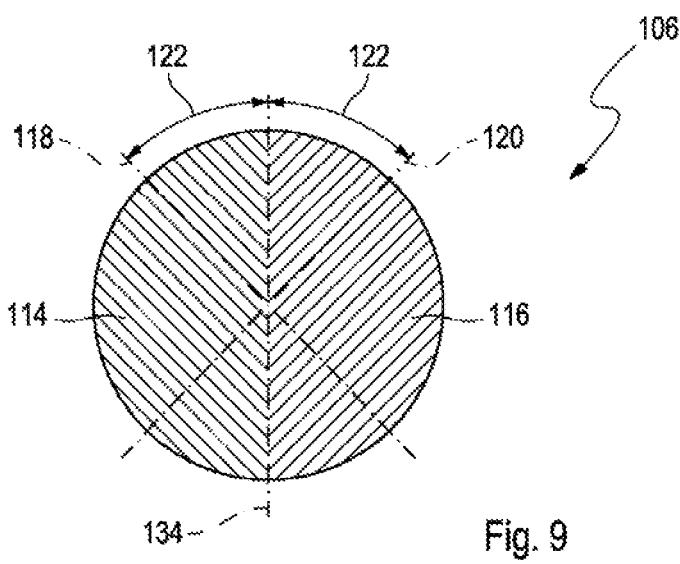
FIG. 9 shows a plan view of a polariser of a polarisation axis measuring device according to an exemplary embodiment of the invention.

The polariser 106 comprises a first region 114 with a first polarisation axis 118 as well as a second region 116 with a second polarisation axis 120, which adjoin one another on the principal axis 134 (illustrated in FIG. 9). In this case the first polarisation axis 118 and the second polarisation axis 120 have with respect to the principal axis 134 an angle which is the same in terms of absolute value 122, preferably between 2° and 5°, particularly preferably between 2.5° and 3.5°, especially preferably 3°. With the mirror 112 the light source 102 can be viewed through the test piece 110, wherein the light is polarised by the polariser 106 through the two regions 114, 116 (illustrated in FIG. 8) of the polariser 106 with divided field of view. In this case the observed brightness depends upon the relative position of the principal axis 134 as the angle bisector between the two polarisation axes 118, 120 of the polariser 106 with respect to the polarisation axis of the test piece 110. For the measurement an adjustment is made to the disappearance of the contrast between the two fields of view preferably in the case of maximum cancellation. Since the brightness of the two fields of view at the boundary is directly discernible, in spite of the manual procedure a high precision and reliability of the measurement can be achieved. After a corresponding calibration the angle of the polarisation axis of the test piece 110 can now be read off directly on the digital display of a connected rotary encoder.

Alternatively the polariser 106 can also be constructed with an undivided field of view and can comprise only one region 114 with a polarisation axis 118, wherein the polarisation axis 118 forms the principal axis 134. In this embodiment the division of the polariser 106 is omitted. In this case the advantage consists in a simpler and more cost-effective design of the polariser 106. In this case the polarisation axis 134 of the polariser 106 is specified as the principal axis thereof. For measurement, there is an adjustment to the minimum or maximum of the transmitted light intensity. Such an embodiment is very suitable in particular for automated methods in which the transmitted light intensity can be detected by a sensor for different angular positions.

Alternatively, instead of a polariser 106 with an undivided field of view a light source with polarised light can be employed. Instead of the polariser 106 with a divided field of view two light sources with polarised light can be employed, the polarisation axes 118, 120 of which are symmetrical with the principal axis 134.

The associated calibration element 10 (illustrated in FIG. 1) for calibration of the polarisation axis measuring device 100 comprises the translucent calibration body 12 made of polarising material, as well as the holder 14 for holding the calibration body 12, which holder 14 has the positioning device 20 for reproducible arrangement in the receptacle 108. The calibration element 10, selectively with the first flat side 26 or with the second flat side 28 directed towards the polariser 106, can be arranged as test piece 110 in the receptacle 108.

Figure 7:
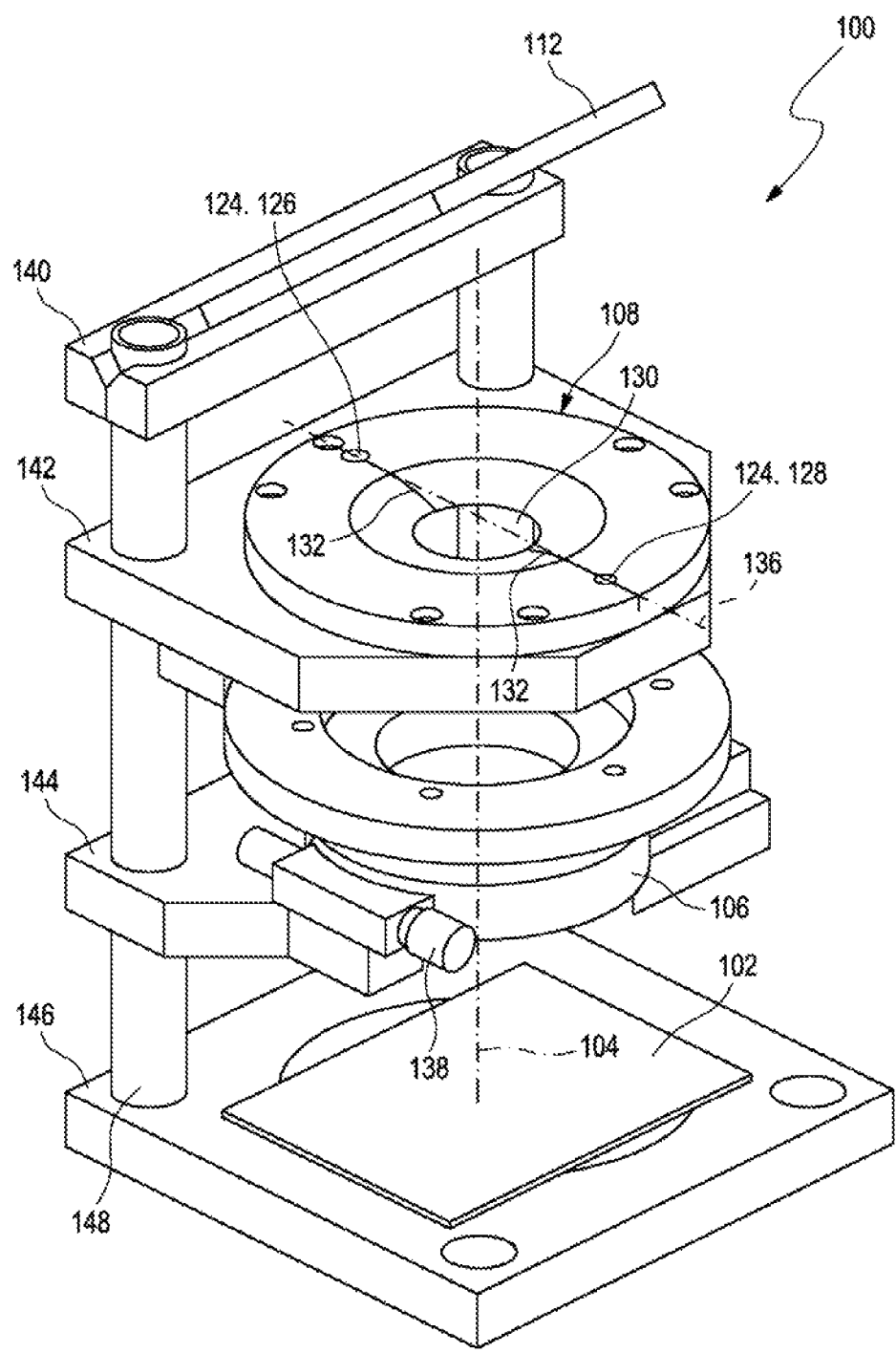
FIG. 7 shows a sectional view of the polarisation axis measuring device of FIG. 6.

FIG. 7 shows an isometric view of the polarisation axis measuring device 100 which is illustrated purely schematically in FIG. 6. The various elements of the polarisation axis measuring device 100 are arranged on a frame 148. The frame 148 is supported by a base plate 146 on which the light source 102 lies centrally. A mounting plate 144 supports the rotary mounting 138 of the polariser 106 with a drive and angle encoder. A further mounting plate 142 supports the receptacle 108 for the test piece 110. The mirror 112 is arranged on a further mounting plate 140 at an angle to the perpendicular of for example 45°. Thus the light beams from the light source 102 can be observed along the optical axis 104 through the polariser 106, through the viewing region 130 of the receptacle 108 and the test piece 110 (not shown) arranged on the receptacle via the tilted mirror 112. By means of the drive of the rotary mounting 138 the polariser 106 can rotate about the optical axis 104 rotate and thus can carry out the equalisation to identical brightness regions of the polariser 106.

FIG. 8 shows a plan view of the receptacle 108 of the test piece 110 of a polarisation axis measuring device 100 according to an exemplary embodiment of the invention. The receptacle 108 has an annular support with an opening 130 as transillumination region. Two counter-elements 124 for the positioning elements 22, 24 of the calibration element 10 are arranged on the support, in order to be able to position the calibration element 10 reproducibly with the aid thereof. In the exemplary embodiment in FIG. 8 the counter-elements 124 are configured as holes 126, 128 in order to receive the locating pins 22, 24 of the calibration element 10 according to FIG. 1. The counter-elements 124 are arranged on an axis 136 of the receptacle 108. Furthermore, markings 132 for reproducible positioning of test pieces 110 are applied to the support of the receptacle 108.

FIG. 9 shows a plan view of the polariser 106 of the polarisation axis measuring device 100 according to an exemplary embodiment of the invention. The polariser 106 comprises a first region 114 with a first polarisation axis 118 as well as a second region 116 with a second polarisation axis 120, which adjoin one another on the principal axis 134. In this case the first polarisation axis 118 and the second polarisation axis 120 have an angle 122 with respect to the principal axis 134 an angle between 2° and 5°, preferably between 2.5° and 3.5°, especially preferably 3°. The angle 122 of the two polarisation axes 118, 120 with respect to the principal axis 134 is shown exaggeratedly in FIG. 9 in order to clarify the effect.

Figures 10, 11:
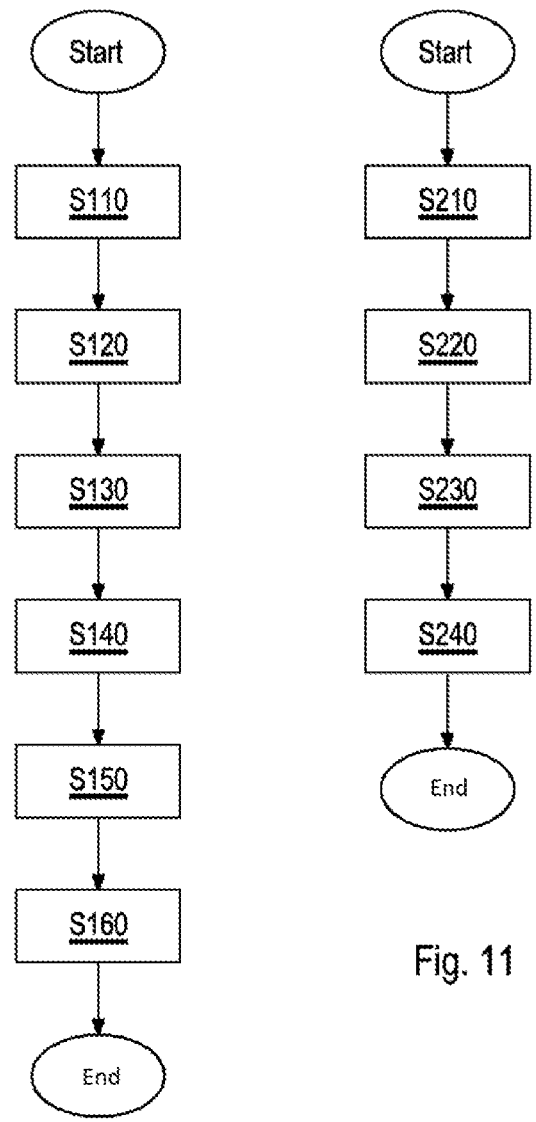
FIG. 10 shows a flow diagram of a method for calibrating a polarisation axis measuring device according to an exemplary embodiment of the invention.
FIG. 11 shows a flow diagram of a method for determining polarisation axes of spectacle lenses according to an exemplary embodiment of the invention.

FIG. 10 shows a flow diagram of the method for calibrating the polarisation axis measuring device 100 according to an exemplary embodiment of the invention. The calibration of the polarisation axis measuring device 100 takes place with the aid of the calibration element 10.

In step S110 the method comprises the insertion of the calibration element 10 into the polarisation axis measuring device 100 with the first flat side 26 directed towards the polariser 106. Then in step S120 in a first rotational position the polariser 106 is aligned with a principal axis 134 in a predefined angular relationship, preferably parallel or perpendicular to a polarisation axis 40 of the calibration element 10, wherein light is transmitted from the first flat side 26 through the calibration element 10. Next, in step S130 the calibration element 10 is inserted into the receptacle 108 with the second flat side 28 directed towards the polariser 106, before in step S140 in a second rotational position the polariser 106 is aligned with a principal axis 134 in a predefined angular relationship, preferably parallel or perpendicular to the polarisation axis 40 of the calibration element 10, wherein light is transmitted from the second flat side 28 through the calibration element 10. Then in step S150 the rotational position of the axis 30 of the calibration element 10 is determined by determining the angle bisector which takes place by arithmetic averaging of the first and second rotational positions of the polariser 106. In step S160 the rotational position of the principal axis 134 of the polariser 106 is assigned a predefined angle value with which it is in the predefined angular relationship with respect to the axis 30 of the calibration element 10 inserted as intended. In this case the reference numerals relate to the elements in FIGS. 1 to 9.

In this case the alignment of the principal axis 134 of the polariser 106 takes place in the steps S120 and S140 by equalising the light intensity transmitted through the first region 114 of the polariser 106 with the first polarisation axis 118 to the same brightness with the light intensity transmitted through the second region 116 of the polariser 106 with the second polarisation axis 120. Alternatively it is also conceivable to carry out the alignment of the principal axis 134 of the polariser 106 by minimising or maximising a light intensity transmitted through a single region 114 of the polariser 106 with the polarisation axis 118.

A pre-calibration in the form of an angle calibration of the rotatably arranged polariser 106 is preferably carried out before the method according to the invention for calibration of the polarisation axis measuring device 100. In the pre-calibration an arbitrarily selected setting/position of the polariser 106 has associated with it a likewise arbitrarily selected angle value. Thus during the rotation of the rotary mounting 138 of the polariser 136 an indication can be given, for example in angle degrees, which can be used afterwards for determination of the polarisation axis 40 of the calibration element 10.

According to an advantageous embodiment of the method according to the invention for calibration of a polarisation axis measuring device 100, a zero value can be assigned to a third rotational position of the principal axis 134 of the polariser 106 in which it is in the predefined angular relationship with respect to the axis 30 of the calibration element 10 inserted as intended. This third position of the polariser 106 advantageously corresponds to an axis defined by markings 132 on the receptacle 108 of the polarisation axis measuring device 100. Thus suitably there is a direct assignment of angle degrees as the relative angular distance of the polarisation axis of the test piece 110 to the axis defined by the markings 132 of the receptacle 108, which enables an advantageous registration and evaluation of the measurement results of the determination of the polarisation axes.

If the axis 30 predefined by the receptacle 108 for the calibration element 10 and the axis 136 predefined by markings 132 for alignment of the test pieces 110 do not correspond, the difference between these two axis positions can be taken into consideration in the assignment of the calibration value. Advantageously in this case the value zero corresponds to the alignment of the principal axis 134 of the polariser 106 parallel or perpendicular to the axis 136 predefined by the marking 132 of the receptacle 108 for the test pieces 110.

A calibration of the polarisation axis measuring device 100 is carried out so that the calibration element 10 is laid onto the receptacle 108 so that the face designated as the front face (for example the first flat side 26) faces upwards. Due to the mechanical fit between the holder 14 of the calibration element 10 and the test piece receptacle 108 a precise alignment on the markings 132 of the receptacle 108 is ensured. Now the position of the polarisation axis 40 should be measured.

Where required the measurement can be carried out several times (n times, at least twice). In this case each time the position of the polarisation axis 40 is read off on the angle indicator and is noted with the displayed plus/minus sign $\varphi_{vor\ 1}$, or $\varphi_{vor\ 2}, \ldots, \varphi_{vor\ n}$.

It is advantageous for the calibration element 10 to be newly placed each time in order to also compensate for any measurement uncertainty resulting from the placing of the calibration element 10.

The position of the polarisation axis 40 in the relative co-ordinates system of the polarisation axis measuring device 100 is then obtained as an average value $$\varphi_{vor} = \frac{1}{n} \times \sum_{i=1}^{n} \varphi_{vori}$$

and the measurement uncertainty is $$u_{vor} = \frac{t}{\sqrt{n \times (n-1)}} \times \sqrt{\sum_{i=1}^{n} (\varphi_{vor} - \varphi_{vori})^2} = \frac{t}{n \times \sqrt{n-1}} \times \sqrt{n \times \sum_{i=1}^{n} \varphi_{vori}^2 - \left(\sum_{i=1}^{n} \varphi_{vori}\right)^2}$$

The value for the correction factor t should be chosen depending upon the required confidence level and the precise number of the individual measurements.

The calibration element 10 is subsequently turned about the specified axis, so that the face designated as the rear face (for example the second flat side 28) faces upwards. The position of the polarisation axis 40 should be measured multiple times as in the last step and the average value $\varphi_{rück}$ as well as the measurement uncertainty $\varphi_{rück}$ should be determined.

The position of the geometric axis of the calibration element 10 in the co-ordinates system of the display of the polarisation axis measuring device 100 is calculated as an average of the positions of the polarisation axes:

$$\varphi_0 = \frac{1}{2} \times (\varphi_{vor} + \varphi_{rück})$$

Thus according to the Gaussian error propagation the calibration uncertainty is $$u_{calib} = \frac{1}{\sqrt{2}} \times \sqrt{u_{vor}^2 + u_{rück}^2}$$

Furthermore, the position of the polarisation axis of the calibration element 10 is obtained on the basis of the geometric axis of the calibration element 10:

$$\alpha_{vor} = \frac{1}{2} \times (\varphi_{vor} - \varphi_{rück})$$

$$\alpha_{rück} = \frac{1}{2} \times (\varphi_{rück} - \varphi_{vor}) = -\alpha_{vor}$$

Where required the values should be in each case rounded to whole hundredths of a degree and the plus/minus sign should be taken into account.

According to a preferred embodiment the subsequent setting of the angle display of the polariser 106 can be carried out as follows. First of all the neutral position is approached with the turntable of the polariser 106. For this purpose the rotary mounting is rotated until the value $\varphi_0$ appears with the correct plus or minus sign in the display. As soon as the value is reached approximately, the exact value is set for example with a fine adjuster. Now the display is set to zero. The precision of the calibration is then $u_{mess} = u_{calib} + u_{anz}$ with $u_{anz} = 0.01°$ as the precision of the display in an exemplary embodiment, which also limits how precisely the rotary mounting can be set to the "true" value. Thus the actual calibration process is finished.

In order to check the calibration, the calibration element can be remeasured.

Advantageously a quick check of the polarisation axis measuring device 100 can be carried out with the calibration element 10 in order to ensure proper functioning of the polarisation axis measuring device 100. For the quick check the calibration element 10 is laid onto the receptacle 108 so that the face designated as the front face (for example the first flat side 26) faces upwards. Due to the mechanical fit between the holder 14 of the calibration element 10 and the test piece receptacle 108 a precise alignment on the markings 132 of the receptacle 108 is ensured. Now the position of the polarisation axis 40 can be measured.

The quick test is deemed to be passed if for example the measured value does not deviate by more than 0.5 degrees from the value predefined for the calibration element 10. If the deviation is greater, the measurement can be repeated. If the value now measured does not deviate by more than 0.5 degrees from the predefined value, the quick test is likewise deemed to be passed. If this is not the case, a second repetition should be carried out. If this likewise proves negative (deviation by more than 0.5 degrees), a precise check should be carried out.

In order to carry out a precise check, the measurements should be carried out from a front face and from a rear face of the calibration element 10 as described in the method according to the invention. The individual measurements should be carried out multiple times (at least three times) in order to reduce the inaccuracy of the test measurements. The device is regarded as properly calibrated, when the absolute values of the values of $\varphi_{vor}$ and $\varphi_{rück}$ correspond within the previously determined measurement uncertainty and the required precision.

FIG. 11 shows a flow diagram of a method for determining polarisation axes of spectacle lenses according to an exemplary embodiment of the invention. In this case spectacle lenses can comprise round blanks, custom-shaped lenses or can be ready mounted in frames, or pairs of spectacle lens and spectacle lens blanks. In the case of spectacle lenses ready mounted in frames the polarisation measuring device 100 preferably has a contact rail (not illustrated), on which the horizontal of the frame or the upper edge of the frame can be contacted in such a way that a respective lens can be arranged above the viewing region 130 of the polarisation measuring device 100. In this case the contact rail takes on the function of the markings 132, which can be omitted in this case.

In step S210 the method comprises the calibration of a polarisation axis measuring device 100 by the method described above. Then in step 220 a spectacle lens is oriented and inserted in the receptacle 108 of the polarisation axis measuring device 100, by aligning it on a marking 132 of the receptacle 108. In step S230 the polarisation axis of the spectacle lens is determined by alignment of a principal axis 134 of a polariser 10 in a predefined angular relationship, preferably parallel or perpendicular to the polarisation axis of the spectacle lens. Subsequently in step S240 an angular difference of the rotational position of the polariser 106 and the marking 132 of the receptacle 108 is determined. From this angular difference it is possible to draw a conclusion as to the polarisation axis of the spectacle lens relative to an orientation of the spectacle lens. Thus the determination of the polarisation axis of the inlaid spectacle lens is concluded and can be transferred for example by means of the previously mentioned contact rail to the spectacle frame.

The polarisation axis measuring device 100 can be coupled to a data processing unit (not illustrated) which contains a program code which is designed to carry out the method for calibration of the polarisation axis measuring device 100 if the program code is executed on the data processing unit. Likewise the data processing unit can contain program code which is designed to carry out the method for determination of polarisation axes of spectacle lenses if the program code is executed on the data processing unit.

The invention claimed is:

1. A method for calibrating a polarisation axis measuring device comprising the following steps:
   (i) insertion of a calibration element into the polarisation axis measuring device and irradiation of a first flat side of the calibration element with polarised light,
   (ii) aligning at least one polarisation direction of the light in a first rotational position with a principal axis in a predefined angular relationship with respect to a polarisation axis of the calibration element,
   (iii) insertion of the calibration element and irradiation of a second flat side thereof with polarised light,
   (iv) aligning at least one polarisation direction of the light in a second rotational position with the principal axis in a predefined angular relationship with respect to the polarisation axis of the calibration element,
   (v) determining the rotational position of an axis of the calibration element by determining an angle bisector between the first and second rotational positions of the polarisation direction of the incident light, and
   (vi) assigning a predefined angle value to the rotational position of the principal axis of the polarisation direction for which the latter is in the predefined angular relationship with respect to the axis of the calibration element inserted as intended,
   wherein a zero value is assigned to a third rotational position of the principal axis of the polarisation direction in the predefined angular relationship with respect to the axis the calibration element is inserted.

2. The method according to claim 1, wherein the predetermined angular relationship is a parallel or perpendicular alignment of the principal axis with respect to the polarisation axis of the calibration element.

3. The method according to claim 1, wherein the insertion of the calibration element into the polarisation axis measuring device takes place with the first flat side thereof directed towards a polariser, which is irradiated with unpolarised light, and wherein for alignment of the polarisation direction of the light incident on the first flat side an alignment of the polariser in a first rotational position with a principal axis takes place in a predefined angular relationship with respect to the polarisation axis of the calibration element and/or alignment of a receptacle for the calibration element,
   wherein the insertion of the calibration element takes place with the second flat side thereof directed towards the polariser, and wherein for alignment of the polarisation direction of the light incident on the second flat side an alignment of the polariser in a second rotational position with the principal axis takes place in the predefined angular relationship with respect to the polarisation axis of the calibration element and/or the alignment of the receptacle for the calibration element, and wherein determining the rotational position of the axis of the calibration element is carried out by determining an angle bisector between the first and second rotational positions of the polariser and assigning a predefined angle value to the rotational position of the principal axis of the polariser, for which the latter is in the predefined angular relationship with respect to the axis of the calibration element inserted as intended.

4. The method according to claim 1, wherein a polariser with a divided field of view is used which comprises at least a first region with a first polarisation axis as well as a second region with a second polarisation axis, which adjoin one another on the principal axis, and wherein the first polarisation axis and the second polarisation axis have with respect to the principal axis an angle which is the same in terms of absolute value with opposite plus/minus signs, wherein the angle is between 2° and 5°.

5. The method according to claim 4, wherein an alignment of the principal axis of the polariser takes place by equalising a light intensity transmitted through the first region of the polariser with the first polarisation axis and a light intensity transmitted through the second region of the polariser with the second polarisation axis to the same brightness, in particular to a low brightness.

6. The method according to claim 1, wherein a polariser is used with an undivided field of view, which comprises at least one region with a polarisation axis, wherein the polarisation axis forms the principal axis.

7. The method according to claim 6, wherein an alignment of the principal axis of the polariser by minimising or maximising a light intensity transmitted through one region of the polariser with the polarisation axis is carried out.

8. The method according to claim 1, wherein the calibration element is irradiated with light from at least one light source which emits polarised light,
   wherein for alignment of the polarisation direction of the light incident on the first flat side an alignment of the light source in a first rotational position with a principal axis takes place in a predefined angular relationship with respect to the polarisation axis of the calibration element, wherein for alignment of the polarisation direction of the light incident on the second flat side the alignment of the light source in a second rotational position with the principal axis takes place in the predefined angular relationship with respect to the polarisation axis of the calibration element, and wherein determining the rotational position of the axis of the calibration element takes place by determining an angle bisector between the first and second rotational positions of the light source and assigning a predefined angle value to the rotational position of the principal axis of the light source, for which the latter is in the predefined angular relationship with respect to the axis of the calibration element inserted as intended.

9. The method according to claim 8, wherein light from two light sources emitting polarised light is directed onto the calibration element, with a first polarisation axis as well as a second polarisation axis, which are arranged symmetrically with respect to the principal axis, and wherein the first polarisation axis and the second polarisation axis have with respect to the principal axis an angle which is the same in terms of absolute value with opposite plus/minus signs, wherein the angle is between 2° and 5°.

10. The method according to claim 9, wherein an alignment of the principal axis of the light sources takes place by equalising the light intensity with the first polarisation axis and the light intensity with the second polarisation axis to the same brightness, in particular to low brightness.

11. The method according to claim 8, wherein one single polarised light source is used with a polarisation axis, wherein the polarisation axis forms the principal axis.

12. The method according to claim 11, wherein an alignment of the principal axis of the light source takes place by minimising or maximising a light intensity with the polarisation axis.

13. The method according to claim 1, wherein as calibration element comprises a translucent calibration body made of polarising material which is transilluminated by the incident light, having a holder for holding the calibration body, which holder has at least one positioning device for reproducible arrangement in a receptacle for a test piece, wherein the holder has a transillumination region for transillumination of the calibration body with light, and wherein the positioning device has at least two diametrically opposed positioning elements, and wherein the calibration element as test piece is inserted into the receptacle of the polarisation axis measuring device selectively with a first flat side or with a second flat side of the calibration body thereof directed towards the polariser.

14. The method for determining polarisation axes of spectacle lenses, comprising the steps of:
(i) calibration of a polarisation axis measuring device with the method according to claim 1,
(ii) oriented insertion a spectacle lens into a receptacle of the polarisation axis measuring device by alignment on a marking of the receptacle,
(iii) determining the polarisation axis of the spectacle lens by alignment of a principal axis of a polariser in a predefined angular relationship with respect to the polarisation axis of the spectacle lens, and
(iv) determining the angular difference of the rotational position of the polariser and the marking of the receptacle and therefrom determining the polarisation axis of the spectacle lens relative to an orientation of the spectacle lens.

15. The method according to claim 14, wherein the predetermined angular relationship is a parallel or perpendicular alignment of the principal axis with respect to the polarisation axis of the calibration element.

16. The calibration element, which is intended for insertion into a receptacle of a polarisation axis measuring device which is designed for carrying out the method according to claim 1, comprising:
a translucent calibration body made of polarising material with a first and an opposing second flat side, and
a holder for holding the calibration body, which holder has at least one positioning device for reproducible arrangement as intended in a receptacle, wherein the holder has a transillumination region for transillumination of the calibration body with light, and wherein the positioning device has at least two opposing positioning elements, wherein the holder with the calibration body is inserted selectively with its first flat side or with its second flat side into the receptacle of the polarisation axis measuring device.

17. The calibration element according to claim 16, wherein the holder for holding the calibration body and the calibration body itself form a component, wherein the holder forms an edge region of the calibration body.

18. The calibration element according to claim 16, wherein the positioning device is configured so that, as intended, the holder is arranged in the receptacle so as to be rotation-proof about an optical axis of the polarisation axis measuring device.

19. The calibration element according to claim 16, wherein the positioning device has at least one pin as positioning element, which projects both over the first flat side and also over the second flat side.

20. The calibration element according to claim 16, wherein the positioning device as positioning element has at least one opening and/or a marking and/or a contact edge, wherein the contact edge forms a component of the circumference of the holder.

21. The calibration element according to claim 16, wherein the calibration body has a translucent region with a polarisation axis.

22. A computer program product for determining polarisation axes of spectacle lenses, comprising a non-transitory computer-readable memory medium containing a program code which is designed to carry out the method according to claim 14, the program code being executed on a data processing unit.

23. The polarisation axis measuring device with a calibration element, which is intended for carrying out the method according to claim 1, and which is intended for insertion into a receptacle of a polarisation axis measuring device, comprising a translucent calibration body made of polarising material with a first and an opposing second flat side, and a holder for holding the calibration body, which holder has at least one positioning device for reproducible arrangement as intended in a receptacle, wherein the holder has a transillumination region for transillumination of the calibration body with light, and wherein the positioning device has at least two opposing positioning elements, wherein the holder with the calibration body is inserted selectively with its first flat side or with its second flat side into the receptacle of the polarisation axis measuring device, comprising:

(i) a receptacle for a test piece,
(ii) a light source with unpolarised light and a polariser with a principal axis, or
(iii) at least one light source with polarised light with a principal axis,
wherein the calibration element has a translucent calibration body made of polarising material, as well as a holder for holding the calibration body, which holder has at least one positioning device for reproducible arrangement in the receptacle,
wherein the calibration element as test piece is inserted into the receptacle selectively with a first flat side or with a second flat side directed towards the polariser.

24. The polarisation axis measuring device according to claim 23, wherein the polariser is arranged rotatably about an optical axis.

25. The polarisation axis measuring device according to claim 23, wherein the receptacle is arranged rotatably about an optical axis.

26. The polarisation axis measuring device according to claim 23, wherein the polariser comprises a divided field of view with at least a first region with a first polarisation axis as well as a second region with a second polarisation axis, which adjoin one another on the principal axis, and wherein the first polarisation axis and the second polarisation axis have with respect to the principal axis an angle which is the same in terms of absolute value with opposite plus/minus signs, wherein the angle is between 2° and 5°.

27. The polarisation axis measuring device according to claim 23, wherein the polariser comprises an undivided field of view with a region with a polarisation axis, wherein the polarisation axis forms the principal axis.

28. The polarisation axis measuring device according to claim 23, wherein the light source comprises at least one first polarisation axis as well as a second polarisation axis, which are arranged symmetrically with respect to the principal axis, and wherein the first polarisation axis and the second polarisation axis have with respect to the principal axis an angle which is the same in terms of absolute value with opposite plus/minus signs, wherein the angle is between 2° and 5°.

29. The polarisation axis measuring device according to claim 26, wherein one single polarised light source is used with a polarisation axis, wherein the polarisation axis forms the principal axis.

30. A computer program product for calibration of a polarisation axis measuring device, comprising a non-transitory computer-readable memory medium containing a program code which is designed to carry out the method according to claim 1, the program code being executed on a data processing unit.

* * * * *